United States Patent [19]

Chadwick et al.

[11] 4,400,538
[45] Aug. 23, 1983

[54] FIXED BED CATALYST FOR MNB AND DNT HYDROGENATION

[75] Inventors: David H. Chadwick, New Martinsville, W. Va.; Thomas E. Boyd, Boulder, Colo.

[73] Assignee: Mobay Chemical Corporation, Pittsburgh, Pa.

[21] Appl. No.: 272,629

[22] Filed: Jun. 11, 1981

[51] Int. Cl.$^3$ .............................................. C07C 85/11
[52] U.S. Cl. .................................... 564/423; 564/305
[58] Field of Search ........................................ 564/423

[56] References Cited

U.S. PATENT DOCUMENTS

| | | | |
|---|---|---|---|
| 4,005,143 | 1/1977 | Bohm et al. .................. | 564/423 X |
| 4,154,705 | 5/1979 | Baldi et al. ................... | 252/466 PT |

FOREIGN PATENT DOCUMENTS

| | | | |
|---|---|---|---|
| 705911 | 3/1965 | Canada ............................... | 564/423 |
| 712193 | 6/1965 | Canada ............................... | 564/423 |
| 774564 | 12/1967 | Canada ............................... | 564/423 |
| 940305 | 10/1963 | United Kingdom ................ | 564/423 |

*Primary Examiner*—John Doll
*Attorney, Agent, or Firm*—Gene Harsh; Joseph C. Gil; Lyndanne M. Whalen

[57] ABSTRACT

The instant invention is directed to a process for the production of an aromatic amino compound of the formula:

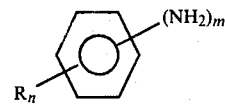

wherein
R is an alkyl substituent of from 1 to about 18 carbon atoms,
m is an integer of from 1 to 3, and
n is an integer of from 0 to 5,
comprising subjecting a nitro compound of the formula:

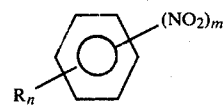

wherein R, m, and n are as defined above, to gaseous hydrogen in the presence of a catalyst, the improvement wherein said catalyst is an activated noble metal in the form of a screen or other coherent body.

4 Claims, No Drawings

FIXED BED CATALYST FOR MNB AND DNT HYDROGENATION

BACKGROUND OF THE INVENTION

Aromatic amino compounds such as aniline and toluene-diamine (TDA) are produced commercially by the catalytic hydrogenation of mononitrobenzene (MNB) and dinitrotoluene (DNT), respectively. These reactions are performed in methanol solution and are generally catalyzed by Raney nickel (Canadian Pat. No. 774,564). These processes necessitate the separation and recovery of the Raney nickel. It is also known to use noble metal catalysts (Canadian Pat. No. 705,911). Rhodium catalysts in the form of granules, sponge, pellets and chunks are also known (Canadian Pat. No. 712,193).

The instant invention overcomes the operation and maintenance costs of the equipment necessary for Raney nickel separation and recovery by the use of fixed bed noble metal catalysts.

DESCRIPTION OF THE INVENTION

The instant invention is directed to a process for the production of an aromatic amino compound of the formula:

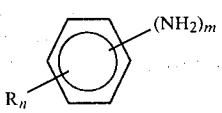

wherein
R is an alkyl substituent of from 1 to about 18 carbon atoms,
m is an integer of from 1 to 3, and
n is an integer of from 0 to 5,
comprising subjecting a nitro compound of the formula:

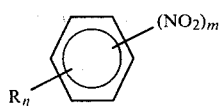

wherein R, m, and n are as defined above, to gaseous hydrogen in the presence of a catalyst, the improvement wherein said catalyst is an activated noble metal in the form of a screen or other coherent body.

With the use of such noble metal catalysts the equipment now used for Raney nickel separation in the recovery is not necessary. Activated noble metal screens (activated in the sense of U.S Pat. No. 4,154,705) proved to be superior to Raney nickel for the production of aniline and toluenediamine in nearly every respect. Reaction temperatures were lower, product quality was better and was not adversely affected by the continued reuse of the catalyst. In addition, the noble metal screen was not affected by typical impurities present in the hydrogenation process as is the case with Raney nickel.

The aromatic nitro compounds with which this invention is concerned are those characterized as nitrobenzene compounds and may be structurally represented by the following formula:

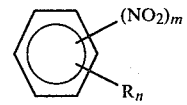

wherein
R is an alkyl substituent of from 1 to about 18 carbon atoms,
m is an integer from 1 to 3, and
n is an integer of from 0 to 5, inclusive.
Specific compounds include the following: nitrobenzene, ortho-nitrotoluene, ortho-nitroethylbenzene, para-nitroethylbenzene, nitroxylenes, (e.g. 4-nitro-orthoxylol, 5-nitro-meta-xylol, and 2-nitro-para-xylol), nitro (2)-mesitylene, 5-nitro-1,2,3,4-tetramethylbenzene, 3-nitro-1,2,4,5-tetramethylbenzene, and para-nitrotoluene.

The noble metal catalysts contemplated by the instant invention are described in detail in U.S. Pat. No. 4,154,705, which is herein incorporated by reference. Specifically, the catalysts of the present invention are in the form of a screen or other coherent body. Suitable coherent bodies include foils, wires, ribbons, metal wools, sheets, perforated and/or fluted and/or dimpled foils or sheets, tubes, blocks or the like or even a honeycomb structure. The catalysts of the present invention have a very large surface area per unit volume. Where large surface areas are desired to be concentrated in one location the surfaces of the present invention can be formed on very fine wire, 0.5 mils thick for example, or on foil or ribbon of such small thicknesses or even thinner, that can be folded or crumpled into a compact mass or on fine metal wool. In general, the catalysts of the present invention are available commercially in the various forms noted above.

The noble metal catalysts which may be used in the instant invention include gold, silver, platinum, palladium, iridium, rhodium, ruthenium, and osmium. Platinum is the preferred catalyst.

In general, the weight of catalyst can vary within wide limits. However, the catalyst should be present in an amount of at least 5% by weight based on the amount of nitro compound in the reaction mixture. It is preferred to use from about 8% to about 18% by weight.

In a general embodiment, the process of the present invention is carried out by contacting an aromatic nitro compound in a suitable solvent, such as methanol, with gaseous hydrogen in the presence of the noble metal catalyst. The theoretical amount of hydrogen is absorbed by the reaction mixture within from 3 to 25 minutes without the use of excessive temperatures or pressure. The process is generally carried out at a pressure between atmospheric pressure and 2000 psi or higher and at a temperature between room temperature and 200° C.

To better describe the present invention, the following illustrative examples are given in detailed description. These examples are by no means to be taken as the only embodiments of the present invention and therefore are not meant to limit the invention in any respect.

EXAMPLES

EXAMPLE 1

A series of consecutive mononitrobenzene (MNB) hydrogenations were run. Unlike Raney nickel, the reaction times observed with the platinum screen decreased before leveling off.

In the first run, one mole equivalent of mononitrobenzene (MNB) (123 g) was charged into a one liter autoclave along with catalyst and 550 ml methanol. For each subsequent run, the same amounts of MNB and methanol were added, while the catalyst remained in the autoclave. The autoclave was pressurized to 900 psi. with hydrogen and stirring and timing begun. As the run proceeded, the time necessary to reach a maximum temperature was noted along with that temperature after the maximum was attained.

After the reaction mixture had cooled to room temperature, it was removed from the autoclave. The reaction mixture was distilled to remove methanol and water. Residues were analyzed gas chromatographically.

An activated platinum screen, 152 mesh, 004 gauge wire, weighing 22 grams was used as a catalyst. Reaction mixtures were removed by means of a sample tube, and fresh reactants were introduced through a port in the autoclave. The results of these experiments are given in Table 1.

TABLE 1

REUSE OF PLATINUM SCREEN IN MNB HYDROGENATION

| Run No. | Reaction Time Min. | Sec. | Temperature Maximum, °C. |
|---|---|---|---|
| 1 | 5 | 45 | 131 |
| 2 | 4 | 50 | 149 |
| 3 | 4 | 25 | 150 |
| 4 | 5 | 30 | 134 |
| 5 | 4 | 56 | 148 |
| 6 | 5 | 8 | 146 |
| 7 | 5 | 3 | 150 |

After a similar series of experiments, the reaction times observed for Raney nickel were consistently much higher. That is, times with Raney nickel leveled off between fifteen and twenty minutes, compared with five minutes observed with the platinum screen.

EXAMPLE 2

The effect of varying the amount of catalyst on yield was investigated in the reduction of MNB. These experiments were performed as described before. The results are summarized in Table 2.

TABLE 2

VARIATION OF CATALYST LEVELS FOR MNB HYDROGENATION CATALYZED WITH PLATINUM SECREENS

| Run No. | Catalyst Weight, g | Reaction Time Min. | Sec. | Aniline |
|---|---|---|---|---|
| 1 | 22 | 6 | 11 | 98.1 |
| 2 | 10.3 | 14 | 30 | 93.0 |
| 3 | 7.3 | 22 | 30 | 85.1 |
| 4 | 3.0 | 43 | 0 | 57.1 |

With reduced levels of catalyst the reaction time increased along with a concomitant decrease in the proportion of aniline in the product.

EXAMPLE 3

An activated platinum plated nickel screen, having a weight of 32 grams was evaluated over a series of runs. Once again reaction mixtures and fresh reactants were moved into and out of the autoclave as described above. These results are shown in Table 3.

TABLE 3

MNB HYDROGENATION CATALYZED WITH PLATINUM PLATED NICKEL SCREEN

| Run No. | Reaction Time Min. | Sec. | Aniline |
|---|---|---|---|
| 1 | 9 | 20 | |
| 2 | 8 | 42 | 96.3 |
| 3 | 8 | 53 | |
| 4 | 9 | 55 | |
| 5 | 11 | 42 | |
| 6 | 9 | 15 | 94.2 |
| 7 | 11 | 15 | |
| 8 | 10 | 45 | |
| 9 | 11 | 55 | |
| 10 | 13 | 15 | 94.6 |

EXAMPLE 4

In a manner similar to Example 1, 91 parts of dinitrotoluene (DNT), 22 parts of the platinum catalyst used in Example 1 and 550 ml of methanol were charged to an autoclave. The autoclave was pressurized to 900 psi with hydrogen. The reaction mixture reached a maximum temperature of 144° C. in about 6 minutes. The resultant product contained in 98.8% toluenediamine.

Although the invention has been described in considerable detail in the foregoing for the purpose of illustration, it is to be understood that such detail is solely for this purpose and that variations can be made by those skilled in the art and without departing from the spirit and scope of the invention except as is set forth in the claims.

What is claimed is:

1. In a process for the production of an aromatic amino compound of the formula:

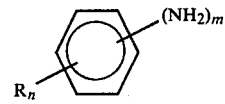

wherein
R is an alkyl substituent of from 1 to about 18 carbon atoms,
m is an integer of from 1 to 3, and
n is an integer of from 0 to 5,
comprising subjecting a nitro compound of the formula;

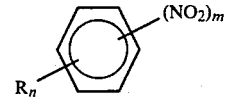

wherein R, m, and n are as defined above, to gaseous hydrogen in the presence of a catalyst, the improvement wherein said catalyst is an activated noble metal in the form of a screen.

2. The process of claim 1, wherein said aromatic amino compound is aniline and said nitro compound is mononitrobenzene.

3. The process of claim 1, wherein said aromatic amino compound is toluenediamine and said nitro compound is dinitrotoluene.

4. The process of claim 1 wherein said catalyst is an activated platinum screen.

* * * * *